United States Patent [19]
Jones et al.

[11] Patent Number: 5,140,990
[45] Date of Patent: Aug. 25, 1992

[54] METHOD OF MEASURING BLOOD PRESSURE WITH A PHOTOPLETHYSMOGRAPH

[75] Inventors: Paul H. Jones, Mercer Island; Wei-Min Wang, Bellevue, both of Wash.

[73] Assignee: SpaceLabs, Inc., Redmond, Wash.

[21] Appl. No.: 656,021

[22] Filed: Feb. 15, 1991

Related U.S. Application Data

[63] Continuation of Ser. No. 579,159, Sep. 6, 1990, abandoned.

[51] Int. Cl.$^5$ ............................................. A61B 5/02
[52] U.S. Cl. .................... 128/665; 128/672; 128/694
[58] Field of Search ............... 128/664–667, 128/672, 694, 713, 687–690

[56] References Cited

U.S. PATENT DOCUMENTS

| | | |
|---|---|---|
| 4,030,485 | 6/1977 | Warner ............................. 128/667 |
| 4,105,021 | 8/1978 | Williams et al. |
| 4,343,314 | 8/1982 | Sramek |
| 4,418,700 | 12/1983 | Warner |
| 4,437,469 | 3/1984 | Djordjevich et al. |
| 4,510,940 | 4/1985 | Wesseling ........................ 128/667 |
| 4,597,393 | 7/1986 | Yamakoski ...................... 128/667 |
| 4,718,428 | 1/1988 | Russell |
| 4,819,646 | 4/1989 | Cheung ........................... 128/666 |
| 4,834,107 | 5/1989 | Warner ............................ 128/666 |
| 4,846,189 | 7/1989 | Sun .................................. 128/667 |

OTHER PUBLICATIONS

Adams et al., "Cuffless Noncannula, Continuous Recording of Blood Pressure," Published in *Surgery*, Jan. 1960, p. 46.

Liu et al., "Estimation of Total Arterial Compliance: An Improved Method in Evaluation of Current Methods," Published in the *American Journal of Physiology*, pp. 588–600, 1986.

*Primary Examiner*—Ruth S. Smith
*Assistant Examiner*—Robert L. Nasser
*Attorney, Agent, or Firm*—Seed and Berry

[57] ABSTRACT

A method and apparatus for determining arterial blood pressures using a photoplethysmograph is provided. In the inventive method the photoplethysmograph output is calibrated to the patient using an auxiliary blood pressure determining instrument, a constant k particular to the patient's arterial blood pressure-volume relationship is determined and is stored for later use; at the time of measurement information is obtained from the photoplethysmograph output; and a computer determines the patient's systolic and diastolic blood pressure.

11 Claims, 8 Drawing Sheets

METHOD OF MEASURING BLOOD PRESSURE WITH A PHOTOPLETHYSMOGRAPH

This application is a continuation of U.S. patent application Ser. No. 07/579,159 filed Sep. 6, 1990, now abandoned under C.F.R. §1.62.

TECHNICAL FIELD

This invention relates generally to blood pressure measurements. More particularly, it relates to a method of non-invasively determining blood pressure using a photoplethysmograph.

BACKGROUND OF THE INVENTION

Arterial blood pressure measurements provide valuable information about a patient's condition. The heart's cyclical action produces a blood pressure maximum at systole, called systolic pressure, and a minimum pressure at diastole, called diastolic pressure. While the systolic and diastolic pressures are themselves important in gauging the patient's condition, other useful parameters are the mean (average) blood pressure during a heart cycle, and the pulse pressure, which is the arithmetic difference between the systolic and diastolic pressures.

The importance of arterial blood pressure has spurred the development of numerous methods of determining it. The most widely used method is probably the familiar blood pressure cuff, which consists of an expandable ring (1) inflated to stop arterial blood flow and (2) then gradually contracted. Using a stethoscope, medical personnel listen to the artery to determine at what pressure blood flow begins, establishing the systolic pressure, and at what pressure flow is unrestricted, establishing the diastolic pressure. More advanced blood pressure monitoring systems plot the arterial blood pressure through a complete heart cycle. Typically, these systems use catheters having piezoelectric pressure transducers that produce output signals dependent upon the instantaneous blood pressure. The output signals are monitored and used to determine the arterial blood pressures over a complete heart cycle. These systems are advantageous in that the blood pressure is continuously measured and displayed.

While prior art methods are useful, they have disadvantages. Cuff-type systems require restricting arterial blood flow and are not suitable for continuous use. The piezoelectric-type systems generally require undesirable invasive techniques, costly disposable materials, and time and skill to set-up. However, during certain critical periods, such as surgery, continuous arterial blood pressure monitoring is highly desirable. Therefore, it would be beneficial to have a method of continuously and non-invasively measuring a patient's blood pressure.

Photoplethysmographs are well-known instruments which use light for determining and registering variations in a patient's blood volume. They can instantaneously track arterial blood volume changes during the cardiac cycle. Since photoplethysmographs operate non-invasively, much work has gone into using them to determine blood pressure. In 1983, inventor Warner was issued U.S. Pat. No. 4,418,700 on a method of determing circulatory parameters, wherein signals from a photoplethysmograph were used to determine arterial blood pressure.

Significant problems were found when investigating the Warner method. Therefore, it is clear that the need for a practical method of continuously and non-invasively monitoring arterial blood pressure has remained.

SUMMARY OF THE INVENTION

It is an object of this invention to provide an improved method for continuously and non-invasively measuring arterial blood pressure.

It is another object of the present invention to provide an improved method and system for non-invasively determining arterial systolic and diastolic blood pressures with a photoplethysmograph.

These and other objects, which will become apparent as the invention is more fully described below, are obtained by providing a method and apparatus for determining arterial blood pressures using a photoplethysmograph. The inventive method comprises the steps of calibrating the photoplethysmograph output with a patient's arterial blood pressure to determine an arterial constant k in the formula, $$\psi = \psi_{inf}(1 - K exp(-kP))$$

where $\psi$ is the arterial blood volume, $\psi_{inf}$ is a conversion constant corresponding to arterial blood volume at infinite pressure, K and k are arterial constants for the patient, and P is the instantaneous arterial blood pressure; gathering data from the photoplethysmograph output during a measurement period; and computing the arterial systolic and diastolic pressures at the measurement period using the evaluated arterial constant k and the data gathered during the measurement period.

DETAILED DESCRIPTION OF THE INVENTION

Figure 1:
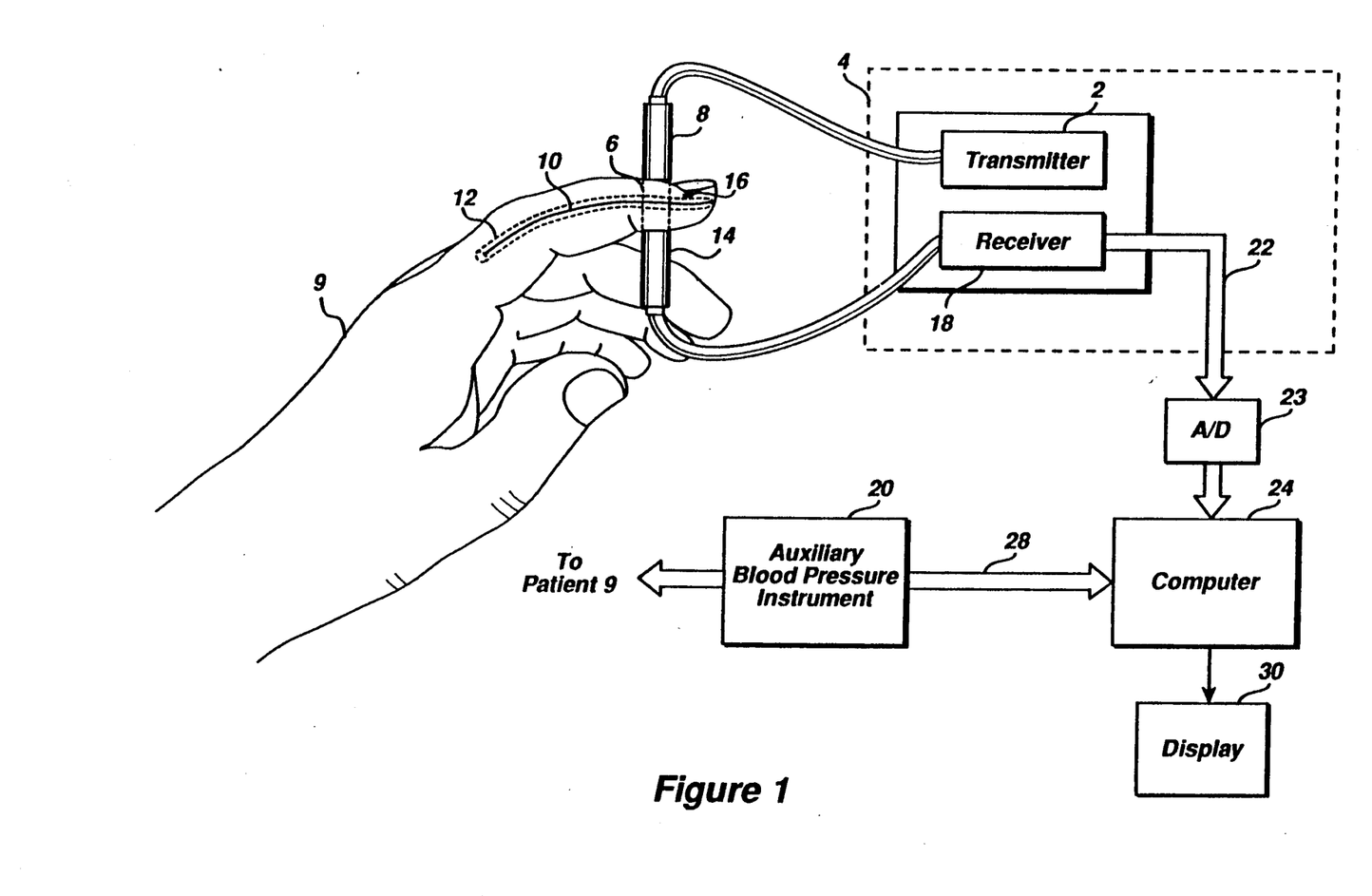
FIG. 1 is a partial cutaway view, partial application depiction, and partial block diagram illustrating a preferred method in operation.

A preferred embodiment of the present invention, shown in FIG. 1, uses a transmitter 2 portion of a photoplethysmograph 4 to cause monochromatic light 6, preferably in the red and IR ranges, to be emitted from a photodiode light source 8. The emitted monochromatic light 6 travels through a patient 9, along a light path which includes blood 10 in an artery 12, to a photodiode light detector 14. While artery 12 has been described, and is shown in FIG. 1, as a single artery, in all practical cases the light path actually passes through many arteries. These arteries can be lumped together and treated as if only one artery 12 existed. Therefore, for simplicity, the remainder of this application will only discuss one artery 12, but it is to be understood that it represents the composite effects of many individual arteries. The light path is also through background tissue 16. The transmitter 2 controls the amount of monochromatic light 6 emitted by varying the amount of current through the light source 8. In the preferred embodiment, the transmitter 2 regulates the monochromatic light 6 at a fixed level.

As the monochromatic light 6 travels along its light path it is partially absorbed by the background tissue 16 and the blood 10. A portion of the monochromatic light 6 is not absorbed and impinges on the light detector 14, creating electrical signals which are applied to a receiver 18 of the photoplethysmograph 4. The magnitudes of these electrical signals depend upon the amount of monochromatic light emitted by the light source 8, the path lengths through the background tissue 16 and the blood 10, the amount of light absorbed per unit length by the blood 10 and tissue 16, the conversion efficiency of the light detector 14, and various lumped losses such as poor focusing of the monochromatic light 6.

Since the artery 12 is pliant, as blood pressure increase so does the volume of blood 10 within the artery 12. As the heart beats, its cyclical action causes the arterial blood pressure to change. This causes the electrical signals to change since the path length through the blood 10 changes, causing the amount of monochromatic light 6 absorbed by the blood 10 to change. Therefore, the electrical signals from the light detector 14 applied to the receiver 18 is a function of the arterial blood pressure.

The receiver 18 amplifies the electrical signals to a usable level and applies them as analog signals, via a receiver line 22, to an analog-to-digital converter A/D 23. The A/D 23 converts the outputs of the receiver 18 to time sampled digital signals which are applied to the computer 24 via a computer bus 25.

Figure 2:
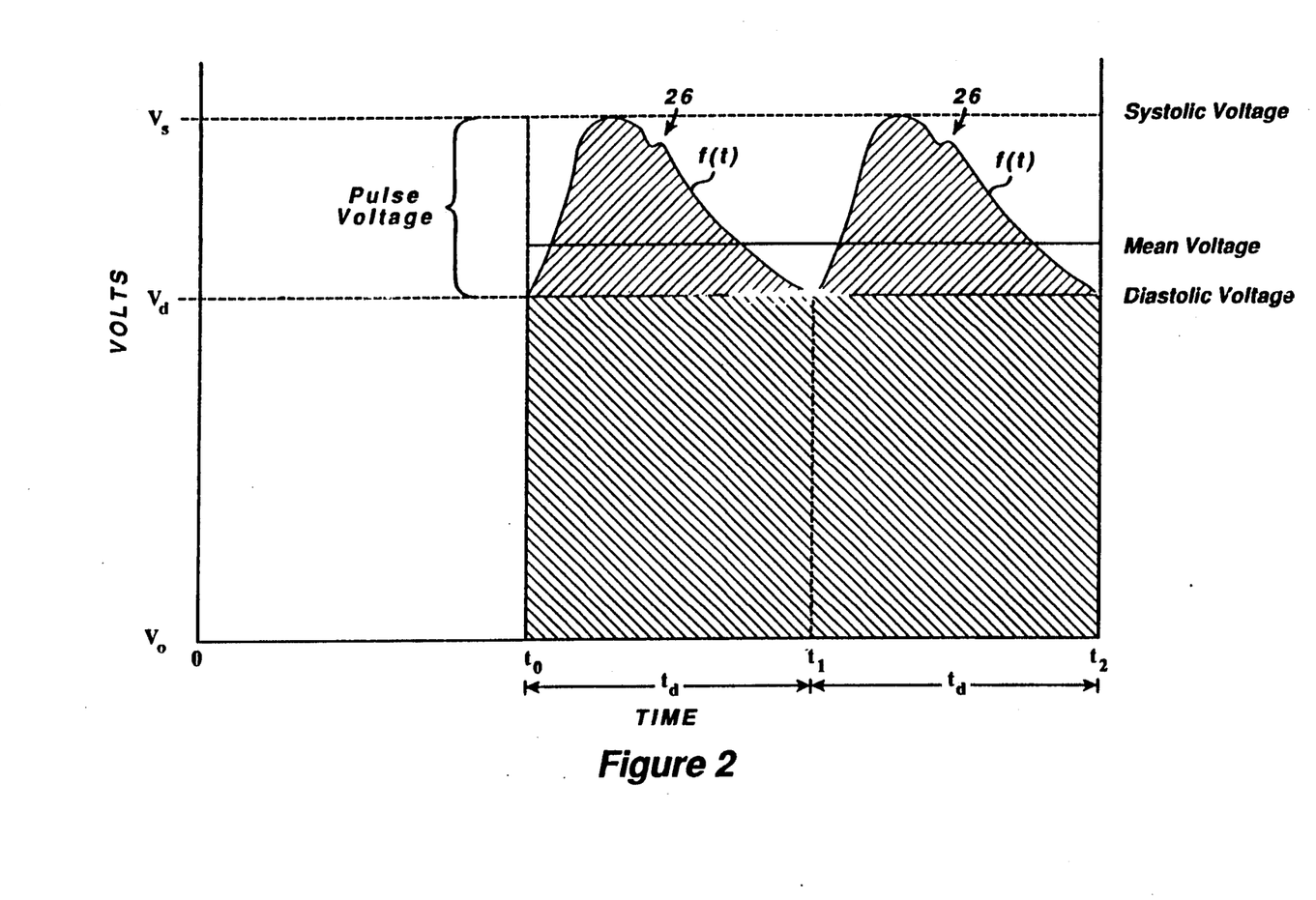
FIG. 2 is a sketch of the output waveform from a photoplethysmograph receiver over two cardiac cycles.

The signals on the receiver line 22 can be represented by the photoplethysmograph output waveform 26, shown in FIG. 2 for two cardiac cycles. The horizontal axis designates time and, in the present apparatus, the vertical axis designates volts, but current levels would also be suitable. Times t0 and t1, denoting the beginning of each cardiac cycle, are clearly marked. The waveform 26 can be described mathematically as a function of time, with the description being f(t). The voltage waveform is inverted from the common pressure waveform because the voltage corresponds to transmitted light. The highest voltage obtained over a cardiac cycle, $V_d$, coincides with the diastolic pressure and the lowest voltage, $V_s$, coincides with the systolic pressure. Between $V_s$ and $V_d$ is a mean pressure voltage $V_m$, which corresponds to the mean, or average, arterial pressure over a full cardiac cycle. The duration of the cardiac cycle, $t_d$ is the time between reoccurrences of the diastolic or systolic voltages. The area between the waveform function f(t) and the diastolic voltage line, shown in crosshatch in FIG. 2, is called the "ARC." The particular values for $V_s$, $V_m$, $V_d$, as well as the waveform function f(t) and the area ARC, change with different patients, photoplethysmographs, sensor locations, and photoplethysmograph settings. However, these parameters are functions of the arterial blood pressure.

Figure 3:
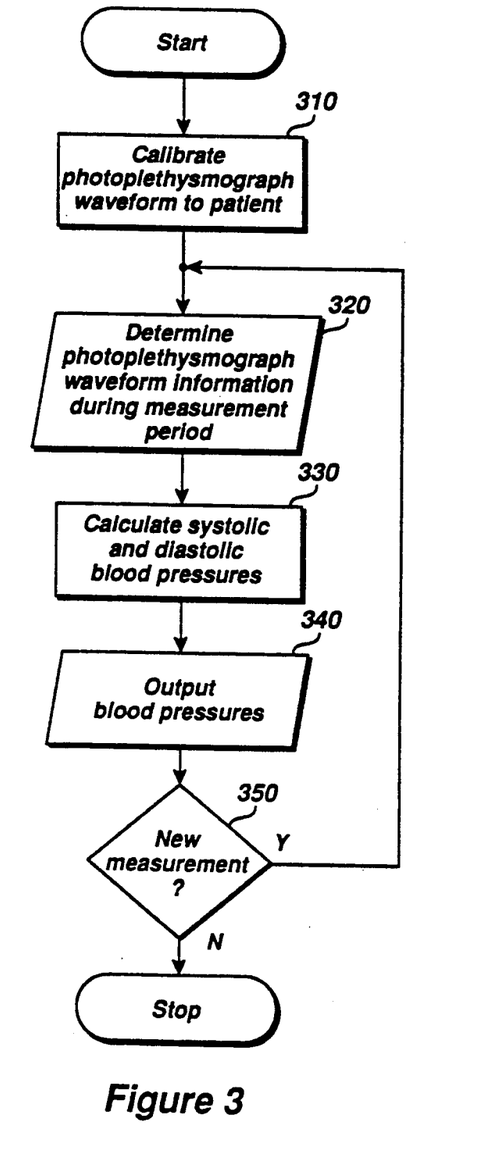
FIG. 3 is a block diagram illustrating the basic procedural steps of the preferred method of FIG. 1.

In a preferred method of the present invention, three major steps are used to determine arterial blood pressure, shown in FIG. 3. The first, shown in block 310, is the calibration of the photoplethysmograph output to the patient. Referring now to FIG. 1, the calibration is accomplished by matching the photoplethysmograph output on the computer bus 25 at the time of calibration with the systolic, $P_s$, and diastolic $P_d$, blood pressures from the auxiliary blood pressure instrument 20. In the preferred embodiment, these blood pressure measurements are entered via a keyboard to the computer 24. However, preferably this information would be entered directly via an instrument bus 28. The photoplethysmograph output is compared with the systolic and diastolic pressures, $P_s$ and $P_d$, from the auxiliary blood pressure instrument 20 and several constants are determined, as is subsequently discussed.

As is shown in FIG. 3, block 320, the next step is the measurement of the photoplethysmograph outputs during a measurement period to determine various information. This information includes the systolic, mean, and diastolic photoplethysmograph voltages $V_s$, $V_m$, and $V_d$, respectively, the cardiac duration $t_d$, and the ARC. The final steps, shown in FIG. 3, blocks 330 and 340, are the calculations of the systolic and diastolic blood pressures, $P_s$ and $P_d$, respectively, using the determined photoplethysmograph information and the constants determined in blocks 320 and 310. After the systolic and diastolic blood pressures are determined, the information is output to medical personnel on a display 30. If more measurements are desired, decision block 350 causes blocks 320, 330, and 340 to be repeated. However, only one calibration phase 310 is required. These major steps are expanded upon below.

DERIVATION OF THE MATHEMATICAL MODEL

The principle of the inventive method is derived from the Beer-Lambert law of analytical chemistry. The Beer-Lambert law gives the relationship between the absorption of monochromatic light by a concentration of a material in a solution as a function of the path length through the solution. Mathematically, the Beer-Lambert law is expressed as:

$$I = I_o \exp^{-cex}$$

where I is the intensity of transmitted light, $I_o$ is the intensity of incident light, c is the concentration of material, e is the extinction coefficient of monochromatic light at a wavelength $\lambda$, and x is the light path length through the medium.

The present invention analogizes blood 10 and tissue 16 density to concentration, modifies the Beer-Lambert law so that the light intensity terms are given in terms of receiver 18 output voltages, and breaks the light path into individual lengths containing the background tissues 16 and the arterial blood 10. Therefore, the modified version of the Beer-Lambert law is:

$$V = ZI_o \exp^{(-c_t e_t x_t - c_a e_a x_a)}$$

where the $t$ refers to the background tissues 16, $a$ refers to the blood 10 in the artery 12, V is an equivalent transmission voltage corresponding to the transmitted light, and Z is a constant relating light intensity to the receiver 18 output voltage.

This can be simplified to:

$$V = A_o \exp(-c_t e_t x_t) \exp(-c_a e_a x_a)$$

where $A_o = ZI_o$.

This version has separable components, $A_o\exp(-c_t e_t x_t)$ which relates to the conversion constant and the background tissues 16, and $\exp(-c_a e_a x_a)$, which relates to the arterial blood 10. For simplicity, the first component can be given as $V_o = A_o\exp(-c_t e_t x_t)$, the background transmission voltage. Therefore, the equivalent transmission voltage can be calculated as:

$$V = V_o \exp(-c_a e_a x_a)$$

It is convenient to express the above formula in terms of arterial blood volume rather than light path length. Therefore, letting $\psi$ be the arterial blood volume, and substituting for the light path $x_a$:

$$V = V_o \exp(-b\psi^{\frac{1}{2}}),$$

where b is equal to $c_a e_a(4/\psi L)^{\frac{1}{2}}$, and L is the light path width through the artery 12. Taking the natural logarithm results in:

$$\ln V = -b\psi^{\frac{1}{2}} + \ln V_o$$

This version becomes more useful after incorporation of the arterial volume-pressure relationship:

$$\psi = \psi_{inf}(1 - K\exp(-kP))$$

where $\psi$ is still the arterial blood volume, $\psi_{inf}$ is a conversion constant corresponding to the blood volume at infinite blood pressure, and K and k are constants for the artery 12, and P is the instantaneous arterial blood pressure. This arterial volume-pressure relationship is a good approximation at the pressures of interest. Substituting this formula for $\psi$ in the logarithmic version:

$$\ln V = -b(\psi_{inf})^{\frac{1}{2}}(1 - K\exp(-kP))^{\frac{1}{2}} + \ln V_o$$

This can be expanded using a Taylor series. Expanding and eliminating higher terms results in:

$$\ln V = f + (n)\exp(-kP)$$

f is equal to $\ln V_o - b(\psi_{inf})^{\frac{1}{2}}$, and n is equal to $(Kb(\psi_{inf})^{\frac{1}{2}})/2$. This can be converted to:

$$V = (u)\exp((n)\exp(-kP))$$

where u is equal to $\exp(f)$. In terms of systolic, diastolic, and mean pressures:

$V_s = (u)\exp((n)\exp(-kP_s))$ for systolic Pressure
$V_d = (u)\exp((n)\exp(-kP_d))$ for diastolic Pressure
$V_m = (u)\exp((n)\exp(-kP_m))$ for mean Pressure
$V_{inf} = u$
$V_0 = (u)\exp(n)$
$V_0/V_{inf} = \exp(n)$ Where $V_{inf}$ is the equivalent receiver voltage at infinite pressure and $V_0$ is the equivalent receiver voltage at zero pressure.

Establishing various ratios:

$V_d/V_s = \exp((n)(\exp(-kP_d) - \exp(-kP_s)))$
$V_d/V_m = \exp((n)(\exp(-kP_d) - \exp(-kP_m)))$
$\ln(V_d/V_s) = (n)(\exp(-kP_d) - \exp(-kP_s))$
$\ln(V_d/V_m) = (n)(\exp(-kP_d) - \exp(-kP_m))$
and
$\ln(V_0/V_{inf}) = n$ leads to useful ratios:

$$\frac{\ln(V_d/V_m)}{\ln(V_d/V_s)} = \frac{\exp(-kP_d) - \exp(-kP_m)}{\exp(-kP_d) - \exp(-kP_s)}$$

$$= \frac{1 - \exp(-kP_p/3)}{1 - \exp(-kP_p)}$$

and:

$$\frac{\ln(V_d/V_s)}{\ln(V_0/V_{inf})} = \exp(-kP_d) - \exp(-kP_s)$$

$$= [\exp(-kP_d)](1 - \exp(-kP_p))$$

where $P_p$ is termed "pulse pressure" and is equal to $P_s - P_d$.

DETAILS OF THE PREFERRED METHOD

The previous section derived various relationships useful in the preferred method as outlined in FIG. 3. The step of calibrating the photoplethysmograph outputs to the patient 9, shown in FIG. 3, block 310 is shown in expanded detail in FIG. 4. The first two steps, shown in block 410 and block 420 are the determination and entering of the systolic and diastolic blood pressures, $P_s$ and $P_d$, respectively, at calibration into the computer 24. As previously indicated and as shown in FIG. 1, these blood pressures are determined by an auxiliary blood pressure instrument 20, preferably an accurate blood pressure cuff having direct inputs to the computer 24 via the instrument bus 28.

Figure 4:
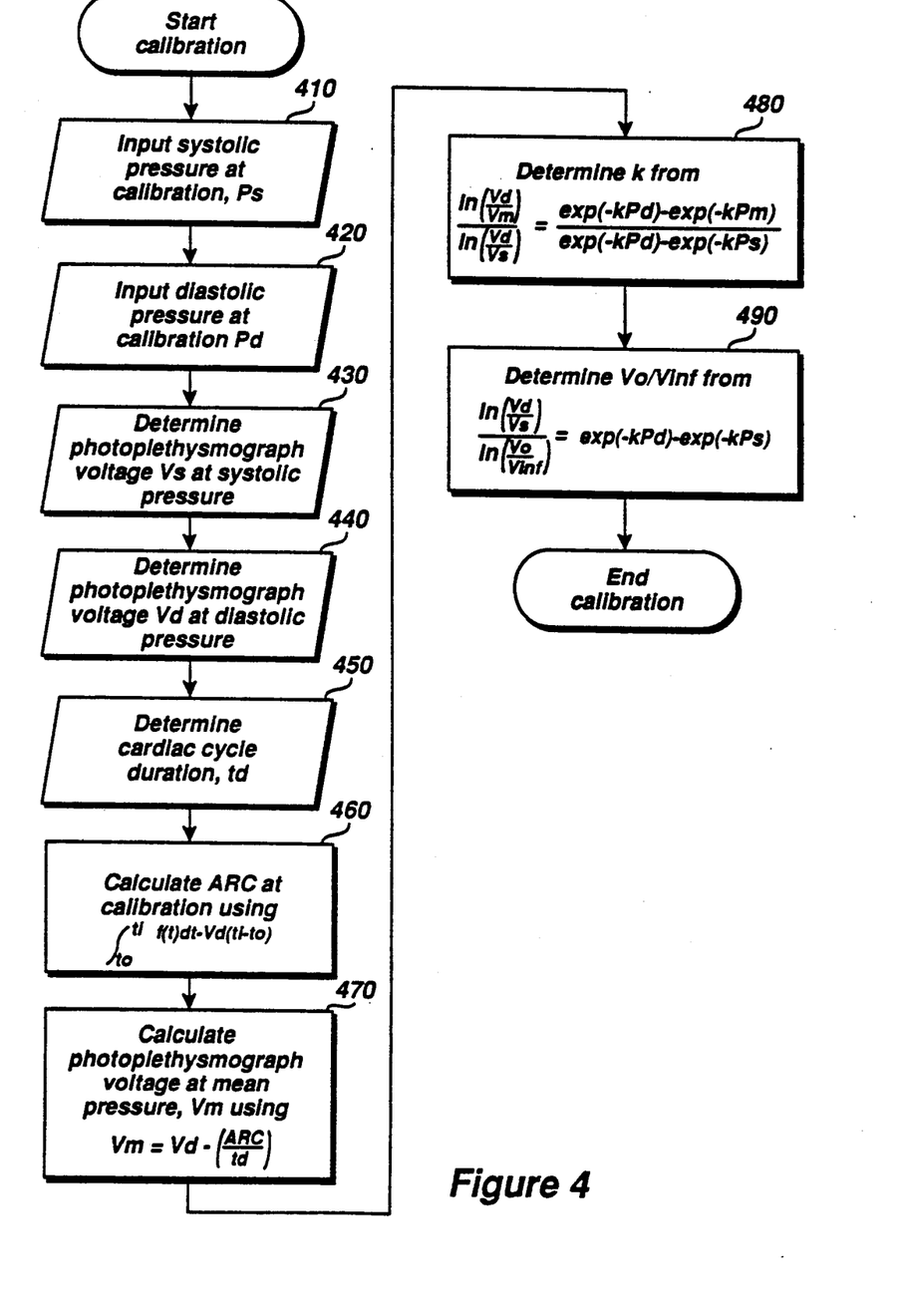
FIG. 4 is a flow diagram of the preferred procedure for calibrating the photoplethysmograph output to a patient according to the inventive method.

The next two steps, shown in blocks 430 and 440 of FIG. 4 are the determination of the photoplethysmograph voltages, $V_s$ and $V_d$, from the receiver 18 output at the calibration systolic and diastolic blood pressures, respectively. These photoplethysmograph voltages are readily determined since they are the minimum and maximum output signals, respectively, from the A/D converter 23. Next, as shown in block 450, the duration of the cardiac cycle, $t_d$ is determined from the output of the A/D converter 23. This is also readily accomplished by using a counter to determine the time between the diastolic voltages, times $t_0$ and $t_1$ of FIG. 2.

To determine various patient arterial constants, the preferred method requires that the area between the diastolic voltage $V_d$ and waveform function f(t), or ARC, be determined. This step is shown in block 460 and is preferably accomplished by determining the integral of the photoplethysmograph voltages over the cardiac cycle using:

$$ARC = (V_d)(t_1 - t_0) - \int_{t_0}^{t_1} f(t)dt$$

where ARC is the area between the waveform f(t) and the diastolic voltage line $V_d$, time $t_0$ is the time at the start of a cardiac cycle, $t_1$ is the time at the start of the next cardiac cycle and $(t_1 - t_0)$ is the cardiac cycle duration $t_d$. The calculation of ARC is easily performed using a digital computer since the output of the A/D converter 23 is a series of digital representations of the photoplethysmograph signals over time. Using the Simpson approximation to determine the integral is particularly expedient because the digital magnitudes can be multiplied by the sampling time between readings, then summed, to arrive at ARC. While ARC is preferably determined using integral equations, other methods of determining it are also acceptable.

Next, as shown in block 470, the photoplethysmograph voltage, $V_m$ corresponding to the mean pressure is determined from the formula $$V_m = V_d - (ARC/t_d);$$

where all terms are as previously given.

With $V_m$ known, the next steps, shown in block 480 and 490, are to determine the patient's arterial constant k, solved numerically, and the ratio $V_0/V_{inf}$ solved using either algebraic or numeric methods:

$$\frac{\ln(V_d/V_m)}{\ln(V_d/V_s)} = \frac{\exp(-kP_d) - \exp(-kP_m)}{\exp(-kP_d) - \exp(-kP_s)}$$

and $$\frac{\ln(V_d/V_s)}{\ln(V_0/V_{inf})} = \exp(-kP_d) - \exp(-kP_s)$$

Figure 5:
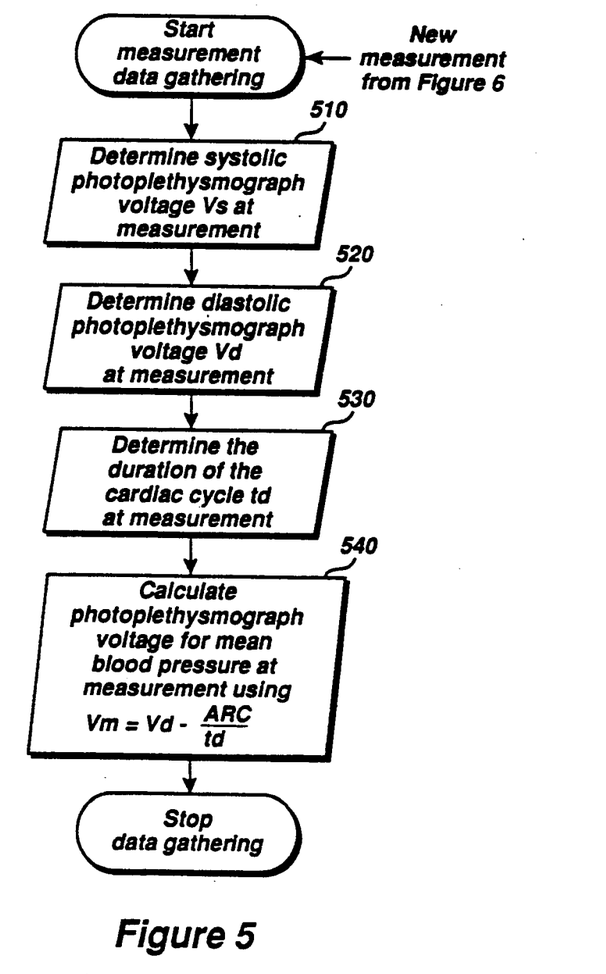
FIG. 5 is a flow diagram of the output monitoring and data acquisition steps according of the inventive method.

With the above patient arterial constant k and $V_0/V_{inf}$ in memory, the patient's arterial blood pressures can be determined only from the photoplethysmograph output. This requires that various information be determined during a measurement period, as shown in block 320 of FIG. 3 and with expanded detail in FIG. 5. Referring to FIG. 5, when arterial blood pressures are to be determined, the computer 24 monitors the photoplethysmograph outputs to determine, at the time of measurement, the systolic voltage $V_s$, the diastolic voltage $V_d$, the duration of the cardiac cycle $t_d$ and the ARC, as shown in blocks 510, 520, 530 and 540, of FIG. 5 respectively. With the information $V_d$, $t_d$ and ARC determined, the computer 24 then determines, as shown in block 550, the equivalent photoplethysmograph voltage $V_m$ using the formula:

$$V_m = V_d - (ARC/t_d)$$

Figure 6:
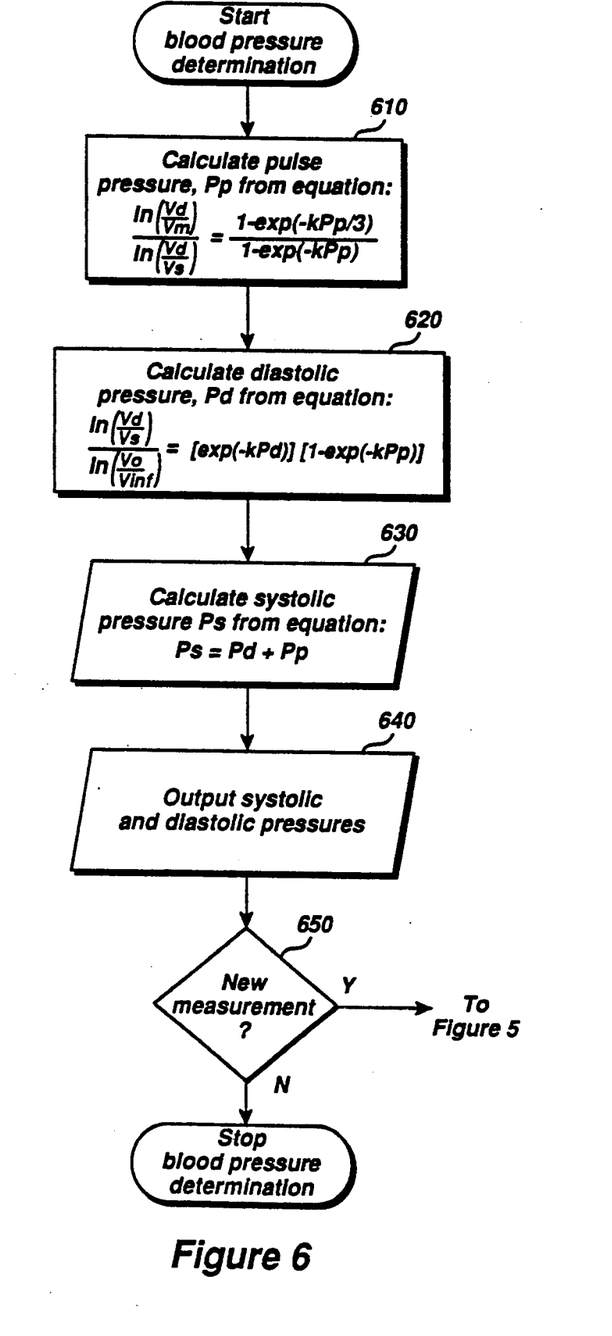
FIG. 6 is a flow diagram outlining the preferred procedural steps for arterial blood pressure determination according to the inventive method.

With the arterial constant k and the ratio $V_0/V_{inf}$ determined according to the flow chart of FIG. 4, and the photoplethysmograph information determined according to the flow chart of FIG. 5, the computer 24 determines the patient's systolic and diastolic blood pressures as shown in the flow chart of FIG. 6, which is a more detailed description of blocks 330 and 340 of FIG. 3. The most efficient method of determining systolic and diastolic blood pressures appears to be, as shown in block 610, to first calculate the pulse pressure $P_p$, using numerical methods, from the formula:

$$\frac{\ln(V_d/V_m)}{\ln(V_d/V_s)} = \frac{1 - \exp(-kP_p/3)}{1 - \exp(-kP_p)}$$

Next, the diastolic blood pressure $P_d$ is determined, as shown in block 620, using the formula $$\frac{\ln(V_d/V_s)}{\ln(V_0/V_{inf})} = [\exp(-kP_d)][1 - \exp(-kP_p)]$$

The determination of the systolic blood pressure $P_s$, is then readily accomplished, as shown in block 630, using the equation $P_s = P_d + P_p$. While the above is the preferred method of calculating arterial systolic and diastolic blood pressures from the photoplethysmograph outputs, other schemes are possible.

The systolic and diastolic blood pressures are then available for output to medical personnel as shown in block 640, in a variety of way such as by digital or analog readouts, chart recorders, voice synthesis, or as in the present embodiment on a display monitor 30. If another set of measurements is desired then decision block 650 causes the flow shown in FIGS. 5 and 6 to be repeated.

The preferred embodiment described above is useful, can be readily implemented on a digital computer, and provides accurate and rapid measurements of arterial blood pressures non-invasively and in a manner suitable for continuous measurements. However, in some patients and under some conditions, the preferred method leads to inaccuracies because of time variations in $V_{inf}$, the equivalent receiver voltage at infinite pressure. $V_{inf}$, in the preferred method was part of the ratio $V_0/V_{inf}$ determined during calibration and presumed constant. The preferred embodiment can be modified to compensate for changes in $V_{inf}$ but at the expense of additional computation difficulty and time.

The alternative embodiment follows the same three major steps as shown in FIG. 3 for the preferred embodiment. However, the calibration procedure of FIG. 4 is modified to that shown in FIG. 7. These calibration procedures, shown in FIG. 7 blocks 710 through 780, are identical until $V_{inf}$ is determined in block 790. It can be shown that $V_{inf}$ is determinable by the following formula:

$$V_{inf} = \exp\{[\ln(V_s) - (\ln V_d)\exp(-kP_p)]/[1 - \exp(-kP_p)]\}$$

Figure 7:
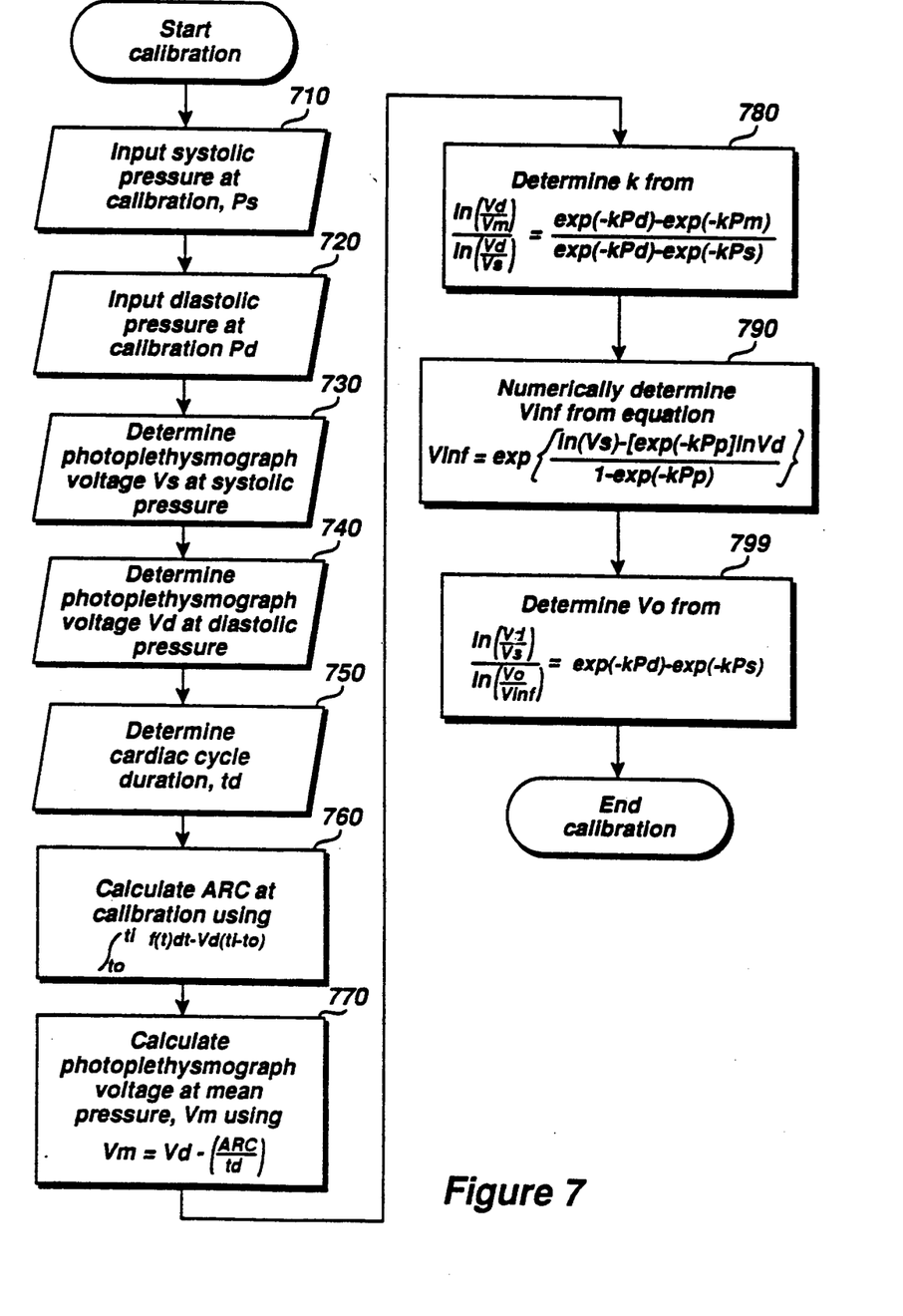
FIG. 7 is a flow diagram of an alternative procedure for calibrating the photoplethysmograph output to a patient according to the inventive method.

With $V_{inf}$ thus determined in block 790, $V_0$, the equivalent receiver voltage at zero pressure, is determined, as shown in block 799, from the formula:

$$\frac{\ln(V_d/V_s)}{\ln(V_0/V_{inf})} = [\exp(-kP_d)][1 - \exp(-kP_p)]$$

After the photoplethysmograph output is calibrated according to the alternative embodiment, as shown in FIG. 7, the patient constants k and $V_0$ are known.

Figure 8:
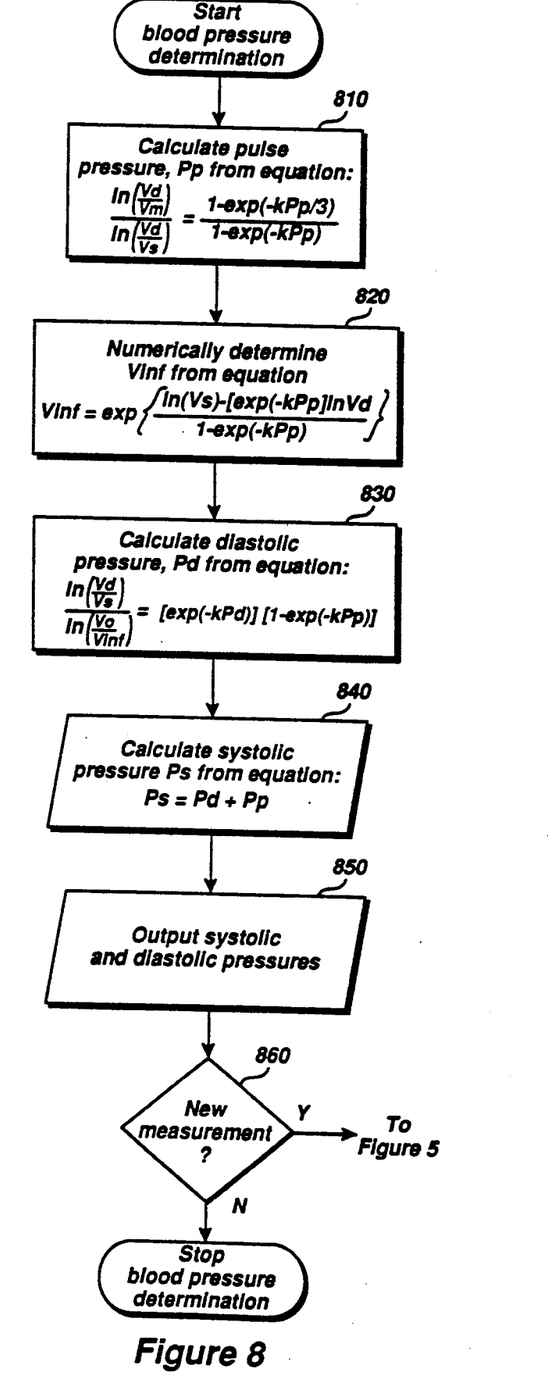
FIG. 8 is a flow diagram outlining alternative procedural steps for arterial blood pressure determination according to the inventive method.

According to the alternative embodiment, the data gathering steps depicted in FIG. 5 remain the same. However, during blood pressure determination, the flow diagram of FIG. 6 is modified to the procedural steps shown in FIG. 8. Referring now to FIG. 8, after determination of the pulse pressure $P_p$ in block 810, in the same manner as it was determined in block 610, the $V_{inf}$ at the time of measurement is determined, as shown in block 820, from equation:

$$V_{inf} = \exp\{\ln(V_s) - [\exp(-kP_p)]\ln V_d\}/[1 - \exp(-kP_p)]\}$$

where $V_s$ and $V_d$ are also the values at the time of measurement.

This new $V_{inf}$ is then used in the equation of block 830, along with the previously stored value of $V_0$, to determine the diastolic pressure $P_d$. This alternative embodiment reduces the effects of changes in $V_{inf}$. The calculation of the systolic pressure $P_s$, shown in Block 840, and the output of the systolic and diastolic pressures, $P_d$ and $P_s$, respectively, as shown in block 850 are performed in the same manner as they were in blocks 630 and 640, respectively, of FIG. 6. Likewise, the decision block 860 operates in the same manner as the decision block 650 in FIG. 6.

The apparatus for practicing the present invention uses a modified pulse oximeter-type photoplethysmograph 4 having numerous user controls, such as receiver 18 gain and light source 8 current settings. It outputs an analog voltage representation of the photodiode output to an analog-to-digital converter A/D 23 which digitizes the receiver 18 output and applies it to an IBM-AT type personal computer 24 under the control of software stored in a hard-disk drive. The display 30 output is on a computer monitor. The required auxiliary blood pressure instrument 20 readings are input by keyboard when directed by software programmed prompts. In future applications, the separate photoplethysmograph 4, A/D converter 23, and computer 24 will probably be replace by similar structures within a single chassis and calibration data will be automatically inputted by an automatic blood pressure cuff.

From the foregoing, it will be appreciated that the invention, as described herein for purposes of illustration, provides an advancement in non-invasive blood pressure instruments. Although alternative embodiments have been described herein, various modifications may be made without departing from the spirit and scope of the present invention. Accordingly, the scope of the invention extends to the broad general meaning of the appended claims.

We claim:

1. A method of determining arterial blood pressures, comprising:

attaching a photoplethysmograph sensor to a patient so that light from said sensor passes through an artery of said patient;

connecting said sensor to a photoplethysmograph, said photoplethysmograph generating an electrical output signal having a predetermined relationship to the volume of blood in said artery;

calibrating said photoplethysmograph during a calibration period by determining the patient's actual arterial blood pressure by means other than said photoplethysmograph, and then determining the value of a first arterial characteristic in a predetermined relationship between said first arterial characteristic, arterial blood volume as indicated by said photoplethysmograph output signal, a conversion constant corresponding to arterial blood volume at infinite pressure, and said actual arterial blood pressure during said calibration period; and analyzing said photoplethysmograph output signal during a measurement period to determine an arterial blood pressure corresponding to said output signal in accordance with said predetermined relationship.

2. The method of claim 1 wherein said conversion constant corresponding to arterial blood volume at infinite pressure is determined by examining the relationship between arterial blood volume and arterial blood pressure, and then determining said arterial blood volume at infinite pressure as the asymptotic value of arterial blood volume in said relationship.

3. The method of claim 1 wherein said predetermined relationship is defined by the formula:

$$\psi = \psi_{inf}(1 - K\exp(kP))$$

where $\psi$ corresponds to the arterial blood volume as indicated by said photoplethysmograph output signal, $\psi_{inf}$ is the conversion constant corresponding to said arterial blood volume at infinite pressure, k corresponds to said first arterial characteristic, K corresponds to a second arterial characteristic, and P corresponds to said actual arterial pressure during said calibration period.

4. The method of claim 1, further including the steps of determining from said photoplethysmograph output signal a value $t_d$ corresponding to the duration of the cardiac cycle during said measurement period, a value S corresponding to systolic pressure during said measurement period, a value D corresponding to diastolic pressure during said measurement period, and a value ARC corresponding to the integral with respect to time of the difference between the photoplethysmograph output signal during said measurement period and a value of said photoplethysmograph output signal corresponding to diastolic pressure.

5. The method of claim 1, wherein said step of calibrating said photoplethysmograph during a calibration period includes the steps of:

determining the actual arterial systolic, diastolic, and mean blood pressures, $P_s$, $P_d$, and $P_m$, respectively, during said calibration period by means other than said photoplethysmograph;

determining values $V_d$ and $V_s$ of said photoplethysmograph output signal corresponding to respective diastolic and systolic arterial pressures during said calibration period;

determining the value $V_m$ corresponding to the mean of said photoplethysmograph output signal during said calibration period; and calculating said first arterial characteristic k from the relationship:

$$\frac{\ln(V_d/V_m)}{\ln(V_d/V_s)} = \frac{\exp(-kP_d) - \exp(-kP_m)}{\exp(-kP_d) - \exp(-kP_s)}$$

where $V_d$ and $V_s$ are respective values corresponding to said photoplethysmograph output signal corresponding to diastolic and systolic pressures during said calibration period, $P_d$, $P_s$, and $P_m$ are respective values corresponding to said actual arterial diastolic, systolic and mean arterial pressures during said calibration period, and k is the value of said first arterial characteristic determined during said calibration period.

6. The method of claim 5, wherein said step of determining a value $V_m$ corresponding to the mean of said photoplethysmograph output signal during said calibration period is accomplished by calculating $V_m$ from the relationship:

$$V_m = V_d - (ARC/t_d)$$

where $V_d$, ARC, and $t_d$ are their respective values corresponding to said photoplethysmograph output signal during said calibration period.

7. The method of claim 1 further including the step of determining from said photoplethysmograph output signal a value X corresponding to arterial pulse pressure during said measurement period by the steps of:

determining values $V_d$ and $V_s$ of said photoplethysmograph output signal corresponding to respective diastolic and systolic arterial pressures during said calibration period;

determining a value $V_m$ corresponding to the mean of said photoplethysmograph output signal during said calibration period; and calculating the value X corresponding to arterial pulse pressure during said measurement period from the relationship:

$$\frac{\ln(V_d/V_m)}{\ln(V_d/V_s)} = \frac{1 - \exp(-kX/3)}{1 - \exp(-kX)}$$

where $V_d$, $V_s$, and $V_m$ are respective values corresponding to said photoplethysmograph output signal corresponding to diastolic, systolic, and mean arterial pressures during said calibration period, and k is the value of said first arterial characteristic determined during said calibration period.

8. The method of claim 7, wherein said step of calibrating said photoplethysmograph during said calibration period further includes the steps of:

determining the actual arterial systolic and diastolic blood pressures, $P_s$ and $P_d$, respectively, during said calibration period by means other than said photoplethysmograph;

calculating the ratio $V_0/V_{inf}$ during said calibration period from the relationship:

$$\frac{\ln(V_d/V_s)}{\ln(V_0/V_{inf})} = \exp(-kP_d) - \exp(-kP_s)$$

where $V_d$ and $V_s$ are respective values corresponding to said photoplethysmograph output signal corresponding to diastolic and systolic arterial pressures during said calibration period, $P_d$ and $P_s$ are respective values corresponding to said actual arterial diastolic and systolic arterial pressures during said calibration period, Vo is a value corresponding to arterial blood volume at zero pressure, Vinf is a value corresponding to arterial blood volume at infinite pressure, and k is the value of said first arterial characteristic determined during said calibration period.

9. The method of claim 8 further including the step of determining from said photoplethysmograph output signal a value D corresponding to diastolic pressure during said measurement period by calculating D from the relationship:

$$\frac{\ln(V_d/V_s)}{\ln(V_0/V_{inf})} = [\exp(-kD)][1 - \exp(-kX)]$$

where $V_d$ and $V_s$ are the respective values corresponding to said photoplethysmograph output signal during said calibration period corresponding to diastolic and systolic pressure, X is a value corresponding to said arterial pulse pressure during said measurement period determined in accordance with the method of claim 7, the ratio $V_0/V_{inf}$ was determined in accordance with the method of claim 8, and k is the value of said first arterial characteristic determined during said calibration period.

10. The method of claim 7, wherein said step of calibrating said photoplethysmograph during said calibration period further includes the step of:

determining $V_{inf}$ at said calibration period from the relationship:

$$V_{inf} = \exp\{[ln(V_s) - (lnV_d)\exp(-kX)]/[1 - \exp(-kX)]\};$$

determining $V_0$ from the relationship:

$$\frac{\ln(V_d/V_s)}{\ln(V_0/V_{inf})} = \exp(-kP_d) - \exp(-kP_s);$$

where $V_d$ and $V_s$ are the respective values of said photoplethysmograph output signal corresponding to diastolic and systolic pressure during said calibration period, $P_d$ and $P_s$ are respective values corresponding to said actual arterial diastolic and systolic pressures during said calibration period, X is a value corresponding to said arterial pulse pressure during said measurement period determined in accordance with the method of claim 7, Vo is a value corresponding to arterial blood volume at zero pressure, Vinf is a value corresponding to arterial blood volume at infinite pressure, and k is the value of said first arterial characteristic determined during said calibration period.

11. The method of claim 10 further including the step of determining from said photoplethysmograph output signal a value D corresponding to diastolic pressure during said measurement period by calculating D from the relationship:

$$\frac{\ln(V_d/V_s)}{\ln(V_0/V_{inf})} = [\exp(-kD)][1 - \exp(-kX)]$$

where $V_d$ and $V_s$ are the respective values of said photoplethysmograph output signal during said calibration period corresponding to diastolic and systolic pressure, X is a value corresponding to said arterial pulse pressure during said measurement period determined in accordance with the method of claim 7, $V_o$ and $V_{inf}$ were determined in accordance with the method of claim 10, and k is the value of said first arterial characteristic determined during said calibration period.

* * * * *